US006071231A

United States Patent [19]

Mendoza et al.

[11] Patent Number: 6,071,231

[45] Date of Patent: Jun. 6, 2000

[54] DEVICE AND METHOD FOR ARTIFICIAL INSEMINATION OF BOVINES AND OTHER ANIMALS

[76] Inventors: Marco Antonio Hidalgo Mendoza, Rebaamen 573, Col. Narvarte 03020, Mexico; William A. Niven, 4011 Guilford Ave., Livermore, Calif. 94550

[21] Appl. No.: 08/893,893

[22] Filed: Jul. 11, 1997

[51] Int. Cl.$^7$ ...................................................... A61B 17/43

[52] U.S. Cl. .................................................. 600/35; 604/96

[58] Field of Search ......................... 600/33–35; 604/906

[56] References Cited

U.S. PATENT DOCUMENTS 5,147,299 9/1992 Mendoza et al. ......................... 604/96

*Primary Examiner*—John P. Lacyk

*Attorney, Agent, or Firm*—Henry P. Sartorio

[57] ABSTRACT

An artificial insemination device is formed by attaching a semen filled straw or tube to one end of a pipette to which a syringe is attached at the other end. An anchorable tip is attached to the other end of the semen filled tube. The semen filled tube is attached by forming tapered bores in the pipette and anchorable tip so that semen filled tubes of various diameters can be press fit into the tapered bores. The pipette-tube-tip assembly is inserted into the animal's vagina using a speculum until the tip enters the cervix, and a seal is formed between the tip and cervix by inflating an attached balloon. The syringe, which contains a diluent fluid, is pushed to force semen and diluent fluid out through ejection port(s) in the tip into the animal's uterus. Optimum amounts of semen and diluent fluid can be delivered to various sized animals.

19 Claims, 4 Drawing Sheets

DEVICE AND METHOD FOR ARTIFICIAL INSEMINATION OF BOVINES AND OTHER ANIMALS

BACKGROUND OF THE INVENTION

1. Field of the Invention

The present invention relates to artificial insemination of bovines and other animals.

2. Description of Related Art

Worldwide, artificial insemination (AI) has penetrated about 80% of the dairy industry but only about 5% of the beef producing industry. One reason is the need for skilled personnel, veterinarians and technicians, trained to grasp the cervix via the rectum and to guide the AI pipette into or through the cervix.

In the traditional method, the inseminator must learn to insert the insemination tube into the cervix by developing the tactile skill to work through the wall of the large intestine while pushing the tube forward through the vagina with the other hand. The cervix is a number of inches long (4–6" in beef cattle), and sometimes has several bends (e.g. “s” or “v” shape in some Brahman cattle), and has several very tight sphincters through which the tube must be guided. Hence there is the ever present danger of perforating the wall of the cervix or the uterus with the inseminating tube, causing injury to the animal. Because of these difficulties, it is often impossible to advance the inseminating tube very far into the cervix, with a corresponding lower insemination efficiency and conception success rate.

For these reasons it normally takes five to six days and two to three cows on which to practice in order to gain an initial skill level. Relatively few who attempt to learn develop a high level of proficiency. Often the practice cows are ruined and must be slaughtered. Also the traditional method of manipulation of the cervix through the large intestine is only practical in large animals such as bovines where the intestine is large enough to be able to introduce the hand and arm. There is no comparable method for small animals such as sheep or goats.

U.S. Pat. No. 5,147,299 to Mendoza et al. describes a device to facilitate the artificial insemination of bovines and other animals. The device allows unskilled persons to learn intracervical semen deposition quickly and effectively without involving rectal penetration and any manipulation of the cervix. The device is inserted into the cervix using a simple illuminated vaginal speculum made of plastic which allows visualization of the cervical opening.

An ordinary inseminating pipette, through which semen is introduced using a syringe, is inserted into one end of a tube which has ejection ports at the other end. A sealing device, e.g. an inflatable balloon, is attached to the side of the tube. The tip is inserted into the cervix, under sight through the speculum, until most of the balloon has disappeared. The balloon is then inflated, forming a seal and anchoring the AI pipette, and semen is injected into the uterus.

While the device has been a great advancement in artificial insemination, reducing time, expenses and effort, and increasing effectiveness, there are still a number of problems. One problem is that the device does not deliver the optimum quantity and concentration of semen that will maximize the probability of conception since there is no way to assure that all of the semen is transferred from its strorage straw into the uterus of the animal without any losses. Another problem is that the device does not make it simple to deliver the optimum total charge of semen and diluting fluid required to accomodate the cervixes and uteruses of animals of varying sizes since there is no way to vary the total charge while preserving the optimum quantity and concentration of semen.

In operation, the frozen semen sample in a common plastic semen storage straw (a plastic tube sealed at both ends containing the semen sample, and stored in a dewar of liquid nitrogen) is warmed and mixed with diluting fluid contained in an ampule. The diluted semen is then loaded into the inseminating pipette by aspirating it out of the ampule, whereupon it is pushed with air from a syringe out of the distal end of the pipette into the uterus of the animal through the anchored tip which is sealed against the cervix to prevent the fluid from leaking back.

Semen is lost at various steps of the operation. Some semen is left behind in the storage straw when it is mixed with the diluting fluid in the ampule. Some semen is also left behind in the ampule when the semen mixed with diluting fluid is aspirated into the pipette. And finally, some semen is left behind in the pipette when the semen mixed with diluting fluid and loaded in the pipette is pushed with air out of the pipette.

These losses of semen produce an inseminating fluid charge with a low sperm concentration and a corresponding low fertilization success rate. In addition, the total charge of semen and diluting fluid cannot be readily adjusted to accomodate the various size cervixes and uteruses found among animals of different sizes, breeds and species. Thus an insemination device with an improved ability of delivering an optimum quantity and concentration of semen, and that lends itself to delivering an optimum total charge of semen and diluting fluid, is desirable.

SUMMARY OF THE INVENTION

Accordingly it is an object of the invention to provide an artificial insemination (AI) device and method for bovines and other animals with improved semen delivery.

It is also an object of the invention to provide an AI device and method which delivers the optimum quantity and concentration of semen.

It is another object of the invention to provide an AI device and method which delivers an optimum total charge of semen and diluting fluid.

It is a further object of the invention to provide an AI device and method which will optimize the fertilization success rate regardless of the varying sizes of the animals.

It is another object of the invention to provide a method and device that can be adapted to other animals.

The invention is an artificial insemination device and method which provides improved transfer of the high concentration of semen contained in a common plastic semen strorage straw into a uterus of an animal with optimum dilution, and with optimal total quantity of semen and diluting fluid. The AI device of the invention is designed so that one end of the semen storage straw is mounted in the pipette which is connected to the syringe. The pipette has a tapered opening at its distal end from the syringe so that one end of the semen storage straw can be press fit into the tapered opening. The anchorable tip of the AI device also has a tapered opening at the end opposite the ejection ports so that the second end of the semen storage straw can be press fit into the tip. Thus the semen in the straw is all pushed forward into the uterus of the animal through its cervix by a controlled amount of dilution fluid with no loss of semen (or sperm).

The invention makes it easy to learn to inseminate in just a few hours. It does not require the need to develop the skill to manipulate the cervix through the wall of the intestine in bovines. The learning period is reduced from a number of days to only a few hours. The invention also allows one to perform artificial insemination with optimum efficiency, delivering the optimum amount of semen and diluent. The invention can also be used with animals of different sizes.

DETAILED DESCRIPTION OF THE INVENTION

The invention is an improvement on the device of U.S. Pat. No. 5,147,299 which is herein incorporated by reference. In the prior device, the anchorable tip is connected to a conventional pipette which is filled with a semen/diluent mixture. In the present invention, a semen storage straw or other semen filled tube is connected to a pipette, and the anchorable tip is connected to the other end of the semen storage straw or tube.

Figure 1:
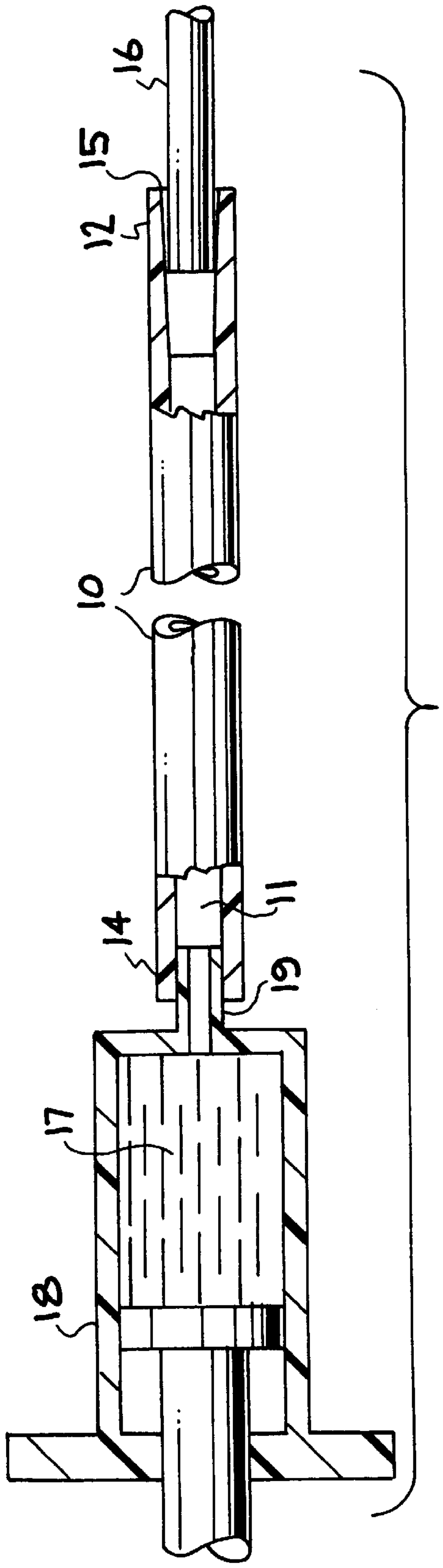
FIG. 1 shows a pipette according to the invention, showing the coupling of a storage straw and a syringe to opposite ends thereof.

FIG. 1 shows an improved inseminating pipette 10 according to the invention, with a specially designed distal end 12 to allow a well sealed attachment of any diameter common plastic semen storage straw 16 and a specially formed proximal end 14 to allow attachment of a syringe. Pipette 10 has a bore 11 which has an outwardly tapering section 15 at the distal end 12. A semen storage straw 16, typically 0.25 cc or 0.5 cc, or any other semen containing tube, is press fit into the tapered or conical section 15 of distal end 12 so that it is securely attached thereto. The tapered section 15 accomodates different diameters of straw 16. Tip 19 of syringe 18 is press fit into bore 11 of pipette 10 at proximal end 14. Syringe 18 contains a predetermined amount of diluent fluid 17, e.g. a 2.9% sodium citrate dilution fluid.

Figure 2:
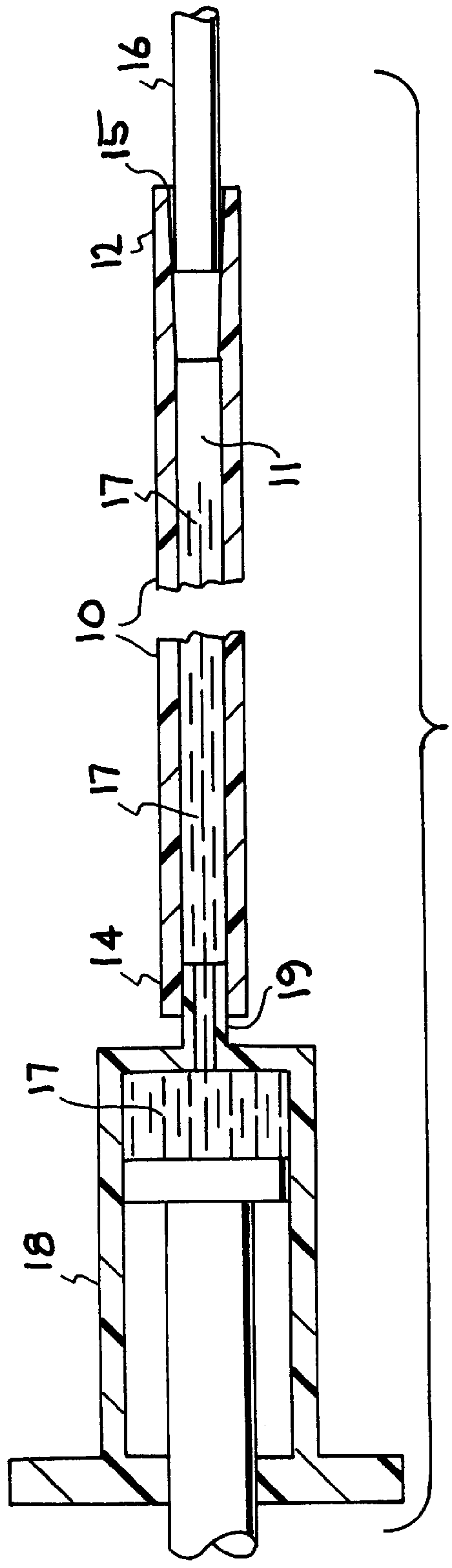
FIG. 2 shows the pipette of FIG. 1 with a controlled amount of dilution fluid injected into the pipette from the syringe.

FIG. 2 illustrates a portion of diluent fluid 17 has been pushed from syringe 18 into bore 11 of pipette 10, but short of tapered section 15 at distal end 12. The amount of fluid 17 is selected to deliver the optimum amount for introduction of semen to the uterus of the animal, and thus will be less for small animals than for large. More or less than the optimum amount will produce less than optimum conception percentages in the animals.

FIG. 3 shows the entire artificial insemination device 29 according to the invention. Semen storage straw 16 filled with semen 21 has been inserted into tapered section 15 of distal end 12 of pipette 10 and a portion of diluent fluid 17 has been pushed from syringe 18 into bore 11 of pipette 10, as in FIG. 2. Inflatable balloon and nozzle assembly 20 has been attached to semen storage straw 16 at the opposite end from pipette 10. Assembly 20 is a hollow tube having an ejection tip 22 at one end and a distal end 23 at the other. Near the ejection tip 22 is mounted an inflatable balloon 24 which is connected to a second syringe 26 through a tube 28 in order to inflate the balloon. The interior channel of assembly 20 includes a tapered or conical section 25 near the ejection tip 22 which is press fit to the other end of semen storage straw 16 from the pipette 10. Tapered section 25 communicates with ejection ports 27 in the ejection tip 22. The distal end 23 of assembly 20 is shown as sliding over end 12 of pipette 10 but may be shorter and not reach pipette 10. Thus straw 16 is positioned between pipette 10 and ejection tip 22 by engagment with tapered sections 15 and 25 respectively.

Figures 3A, 3B:
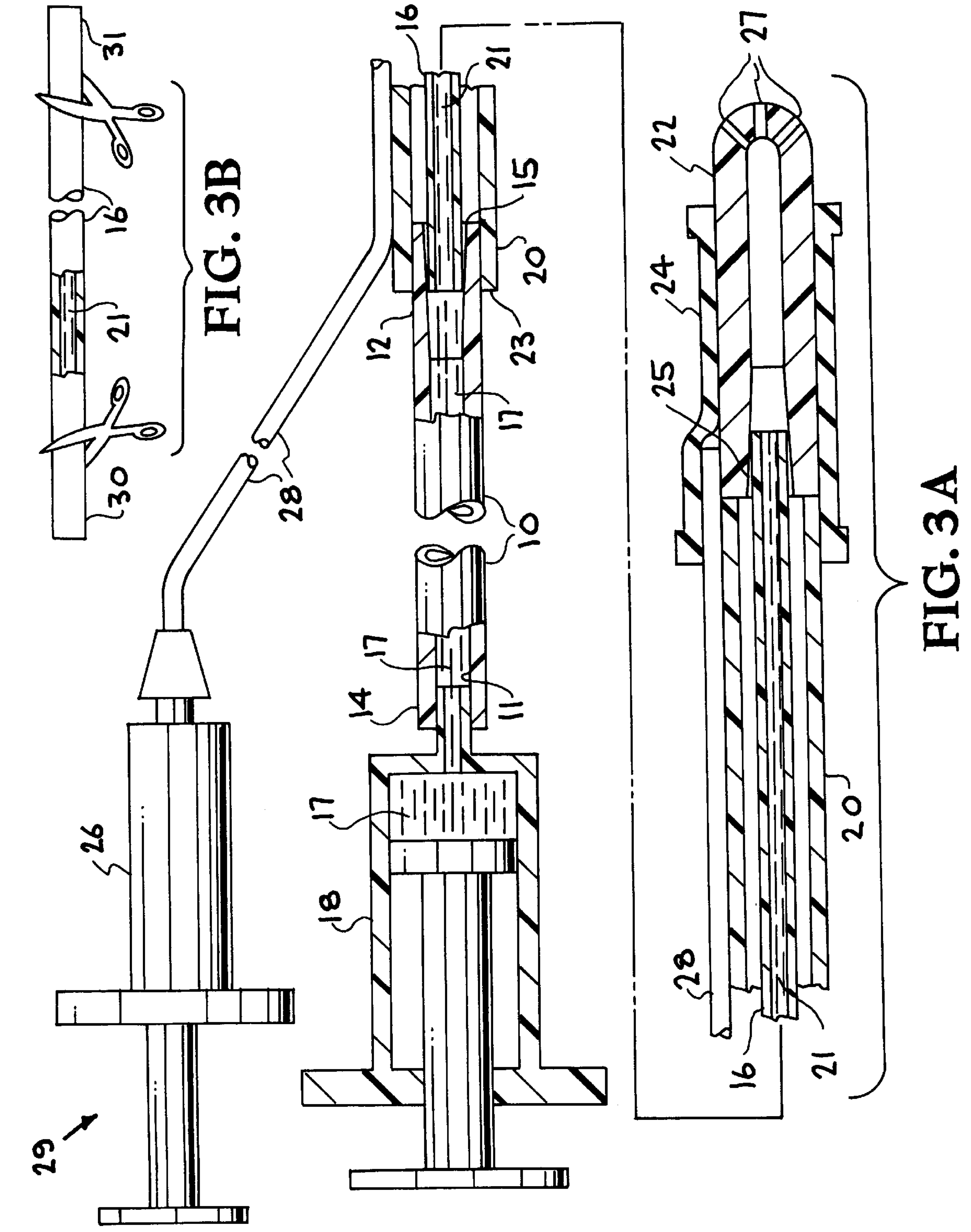
FIG. 3A shows an entire artificial insemination assembly, showing a semen storage straw mounted to a pipette at one end as in FIGS. 1 and 2, and to an anchorable tip at the other end as in FIGS. 4 and 5.
FIG. 3B shows a semen storage straw and the cuts made to insert the straw into the artificial insemination assembly.

FIG. 3B shows the procedure of first cutting end 30 of semen storage straw 16 after the semen has been thawed, and then cutting end 31 after end 30 has been tightly fit into end 12 of pipette 10. End 31 is then fit into section 25 of assembly 20. Of course, the straws are cut very near the ends so that little semen is lost.

While the straw is typically a common plastic semen storage straw, typically 0.25 cc or 0.5 cc, any other tube-like presentation, such as the mini-tube used in Germany, can also be used. A pellet presentation of the semen can also be used where the pellet is first thawed, diluted and loaded into an inseminating straw which is then used in the AI apparatus.

Figure 4:
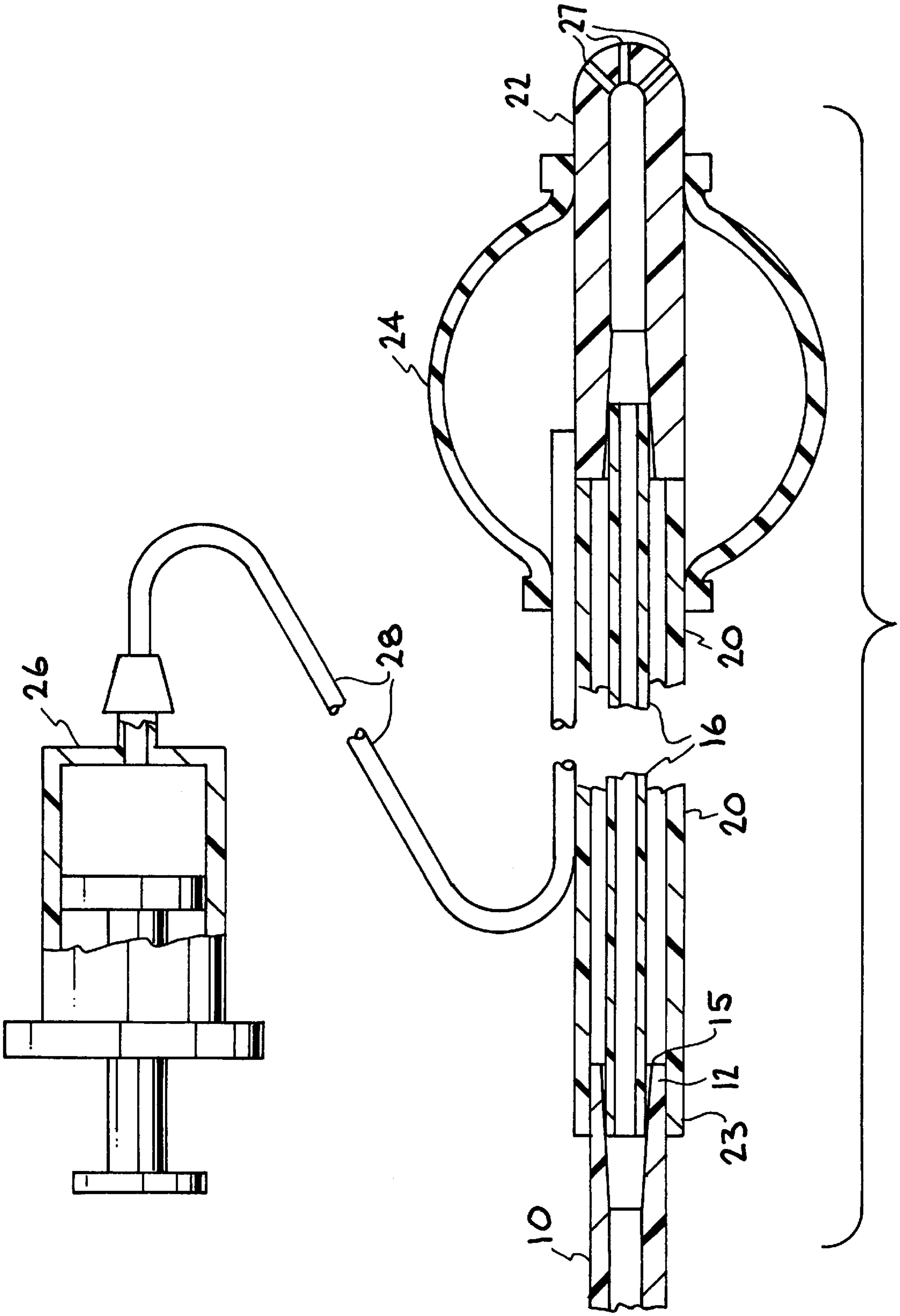
FIG. 4 shows the entire artificial insemination assembly, including the anchorable tip with ejection ports and inflated balloon for anchoring in the cervix.

FIG. 4 shows the assembly 20 of ached to pipette 10 by straw 16 wherein balloon 24 has been inflated with air from syringe 26 through flexible tube 28 so as to form a seal with the cervix of the animal's uterus. Although an inflatable balloon is preferred, other sealing devices, e.g. a permanently inflated balloon, can also be used. Once the device has been positioned, syringe 18 will be used to push diluent 17 into the pipette and straw 16, thereby forcing the semen and diluent fluid toward tip 22.

Figure 5:
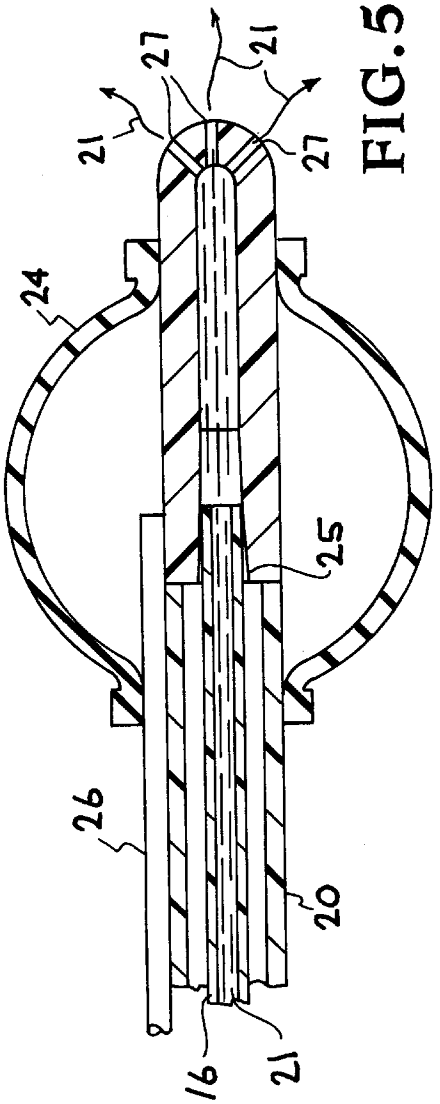
FIG. 5 shows the anchorable tip of the artificial insemination assembly, showing ejection of semen from the ejection ports.

FIG. 5 shows the ejection of semen and diluent from ejection ports or orifices 27 in tip 22. Multiple ejection ports 27 are positioned at the apex and on lateral sides of tip 22. Although one port may be sufficient, multiple ports are preferable. The tip 22 may be configured as shown in U.S. Pat. No. 5,147,299. As syringe 18 is pushed, diluent fluid is pushed forward into straw 16 thereby pushing semen forward to tip 22 where it is ejected into the uterus of the animal. As the syringe 18 continues to be pushed all the way down, all the semen and most of the diluent fluid will be ejected, providing the optimum amount of semen and diluent. In order to deliver the optimum amount of diluent, the amount of diluent initially placed in the syringe should therefore be greater than the desired amount by the amount that will fill the artificial insemination device.

Figure 6:
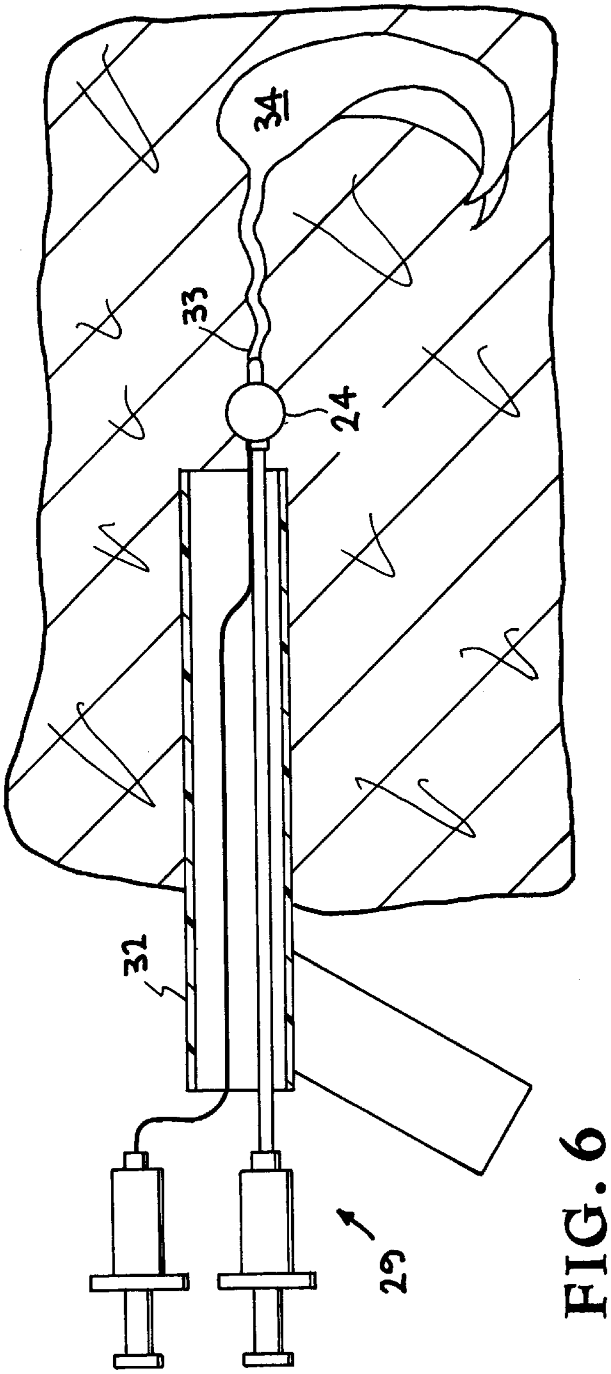
FIG. 6 shows the AI device in operation in a bovine using a speculum for positioning.

FIG. 6 shows the artificial insemination device in operation in a bovine. With the aid of a plastic lighted speculum 32 to open the animal's vagina and view the interior, the device 29 is pressed part way into the cervix 33, the balloon 24 is inflated to form a seal with the cervix, and the dilution fluid is forced out of the syringe, pushing the semen sample and diluent into the uterus 34.

Thus the invention provides a method and apparatus for artificial insemination of bovines and other animals which delivers the optimum quantity and concentration of semen, and an optimum total charge of semen and diluting fluid. Various diameters of common semen storage straws and other semen filled tubes can be accomodated. Non-experts can easily learn to artificially inseminate, and to do so with high efficiency.

Changes and modifications in the specifically described embodiments can be carried out without departing from the scope of the invention which is intended to be limited only by the scope of the appended claims.

The invention claimed is:

1. Apparatus for the artificial insemination of bovines and other animals, comprising:

a pipette having a first end adapted to receive a syringe and a second end comprising a section having a tapered bore adapted to receive one end of a semen filled tube;

an anchorable tip adapted to receive a second end of the semen filled tube and having at least one ejection port.

2. The apparatus of claim 1 wherein the anchorable tip contains a channel having a tapered bore adapted to receive the second end of the semen filled tube.

3. The apparatus of claim 1 wherein the anchorable tip further comprises a device to form a seal with the cervix of the animal.

4. The apparatus of claim 3, wherein the device to form a seal is an inflatable balloon.

5. The apparatus of claim 4, further comprising a device attached to the balloon to inflate the balloon.

6. The apparatus of claim 1 wherein the anchorable tip has at least one ejection tip on a lateral side thereof.

7. The apparatus of claim 1 and further comprising a syringe connected to the first end of the pipette and containing a predetermined amount of diluent fluid.

8. The apparatus of claim 1 and further comprising a semen filled tube having a first end fittingly engaged in the second end of the pipette and a second end fittingly engaged in the anchorable tip.

9. Apparatus for the artificial insemination of bovines and other animals, comprising:

a pipette having a bore therethrough;

a syringe connected to a first end of the pipette;

a semen filled tube open at both ends and having a first end connected to a second end of the pipette;

an anchorable tip having a bore therethrough and at least one ejection port communicating with the bore of the anchorable tip, a second end of the semen filled tube being connected to the anchorable tip;

the pipette, semen filled tube and anchorable tip defining a flow path from the syringe to the at least one ejection port.

10. The apparatus of claim 9, wherein the second end of the pipette comprises a section wherein the pipette bore is tapered to receive the first end of the semen filled tube and the anchorable tip comprises a section wherein the anchor tip bore is tapered to receive the second end of the semen filled tube.

11. The apparatus of claim 10, wherein the ends of the semen filled tube are press fit into the tapered bores of the pipette and anchorable tip.

12. The apparatus of claim 9, wherein the semen filled tube is a plastic semen filled straw.

13. The apparatus of claim 9, wherein the anchorable tip further comprises a device to form a seal with the cervix of the animal.

14. The apparatus of claim 13, wherein the device to form a seal is an inflatable balloon, and further comprising a device attached to the balloon to inflate the balloon.

15. Method for the artificial insemination of bovines and other animals, comprising:

providing a pipette having a first end adapted to receive a syringe and a second end adapted to receive one end of a semen filled tube;

connecting the syringe to the first end of the pipette;

inserting a first open end of the semen filled tube into the second end of the pipette to attach the tube to the pipette;

providing an anchorable tip adapted to receive a second end of the semen filled tube and having at least one ejection port;

inserting a second open end of the semen filled tube into the anchorable tip to attach the tip to the tube;

guiding the pipette with attached semen filled tube and anchorable tip into the animal's vagina until the anchorable tip is inserted into the cervix;

forming a seal between the anchorable tip and cervix wall behind the at least one ejection port;

pushing the syringe to eject semen from the semen filled tube through the at least one ejection port into the uterus of the animal.

16. The method of claim 15, further comprising forming the second end of the pipette with a bore which is tapered to receive the first end of the semen filled tube and forming the anchorable tip with a bore which is tapered to receive the second end of the semen filled tube.

17. The method of claim 16, further comprising press fitting the ends of the semen filled tube into the tapered bores of the pipette and anchorable tip.

18. The method of claim 15, wherein forming the seal between the anchorable tip and cervix wall is performed by inflating a balloon attached to the anchorable tip.

19. The method of claim 15, further comprising inserting a speculum into the animal's vagina to visually locate the cervix and guiding the pipette with attached semen filled tube and anchorable tip into the vagina through the speculum.

* * * * *